United States Patent [19]

Owen

[11] Patent Number: 5,185,450

[45] Date of Patent: Feb. 9, 1993

[54] TETRAZOLIUM COMPOUNDS FOR CELL VIABILITY ASSAYS

[75] Inventor: Terence C. Owen, Tampa, Fla.

[73] Assignee: University of South Florida, Tampa, Fla.

[21] Appl. No.: 899,155

[22] Filed: Jun. 12, 1992

Related U.S. Application Data

[63] Continuation of Ser. No. 657,462, Feb. 19, 1991, abandoned.

[51] Int. Cl.⁵ .................. C07D 417/04; C07D 251/01

[52] U.S. Cl. .................. 548/194; 548/250; 548/252; 548/193; 548/112

[58] Field of Search ............... 548/252, 204, 193, 194, 548/112

Primary Examiner—David B. Springer
Attorney, Agent, or Firm—Reising, Ethington, Barnard, Perry & Milton

[57] ABSTRACT

Novel tetrazolium salts, which are biologically reducible to blue water-soluble formazan compounds by living cells, are utilized in cell culture viability assays.

8 Claims, No Drawings

TETRAZOLIUM COMPOUNDS FOR CELL VIABILITY ASSAYS

This is a continuation of copending application Ser. No. 07/657,462 filed on Feb. 19, 1991, now abandoned.

TECHNICAL FIELD

The present invention generally relates to the use of tetrazolium salts in assays to distinguish living cells from dead cells. More particularly, the invention provides novel tetrazolium compounds for cell viability assays and their method of use.

BACKGROUND OF THE INVENTION

The biological reduction of a colorless tetrazolium salt 1 to a colored formazan 2 is widely used to indicate and measure cell viability in cell cultures (1,2).

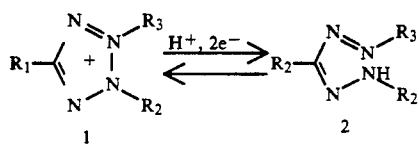

Numerous laboratories have consequently used tetrazolium salts for many years in assays to distinguish living cells from dead ones. There are several characteristics which suit tetrazolium salts to this purpose.

Tetrazolium salts are reduced to the intensely colored formazans by the functioning electron transport systems of viable cells, either directly or through the intermediacy of electron carriers such as phenazine methosulfate or menadione. The direction of the color change, from the colorless oxidized form to a colored reduced form, is practically unique among dye-stuffs. Viable cells develop color in direct proportion to their metabolic activity. The colorless tetrazolium reagent is an ionized salt, soluble in water and capable of passing into cells. The colored reduction product, the formazan, is not ionic, is insoluble in water, and is deposited within viable cells in a manner well suited to histochemical evaluation. A number of different structural groups can be attached to the tetrazolium core to influence color, redox potential, solubility, and histochemical characteristics of the tetrazolium - formazan couples.

Over a thousand different tetrazolium compounds have been synthesized of which about a dozen are in common use for cell viability assays. Some of the procedures using tetrazolium salts currently in vogue have problems in that they are cumbersome, labor intensive, and ill-suited to volume throughput or automation. Typically, in such prior art procedures the formazan dye is deposited as an insoluble precipitate within cells of the culture which, in the standard procedure, must be spun down, mounted on a microscope slide, and evaluated (rather subjectively) by a skilled microscopist. Recently procedures have been described in which the cells are lysed with solvents such as DMF, DMSO, and 2-propanol, and the dye thereby brought into solution to be measured spectrophotometrically (3,4). These procedures give less subjective quantitation, but are no more convenient nor less labor intensive than the earlier methods.

One tetrazolium compound used recently for cell viability assays is the tetrazolium disulfonic acid XTT, a tetrazolium disulfonic acid wherein $R_1$=carbanilido, and $R_2$=$R_3$=2-methoxy-4-nitrobenzene5-sulfonic acid (5). An assay utilizing this compound capitalizes on the water solubility of the formazan disulfonic acid produced upon reduction of the tetrazolium zwitterion-salt. The dye diffuses out of the cells in which it is produced and into the culture medium. Optical density is read directly. The steps involving removal of the medium and extraction with solvent are obviated and the procedure becomes amenable to full automation.

There are problems with XTT however. The synthesis for XTT is problematic and the XTT formazan is yellow-orange in color (in water), leading to difficulties in the differentiation of the formazan from a generally yellow cell culture medium background. Problems also arise in certain cell types where XTT forms precipitates.

To be most useful in spectrophotometric assays, a formazan should be purple, blue or violet. XTT shows that there is an advantage in utilizing a tetrazolium compound which reduces to a water soluble formazan which is capable of diffusing out of the cells into the culture medium where it could be measured by standard spectrophotometers, and also the utility of sulfonate groups in achieving such water solubility in the formazans. The present invention provides these advantages while further providing structural flexibility allowing chemical modification to overcome many of the problems associated with XXT.

SUMMARY OF THE INVENTION

In accordance with the present invention, there is provided a tetrazolium compound having attached to the tetrazolium ring either (a) at least one side chain capable of having at least two acidic groups thereon for rendering the compound water soluble: or (b) at least two side chains each capable of having one or more acidic groups thereon for the same purpose of rendering the compound water soluble.

The present invention further provides a cell viability assay including the steps of exposing cells to the above described tetrazolium compound, the viable cells reducing the compound to a blue or purple water soluble formazan and detecting the blue or purple color of the formazan in the media as an indication of cell viability.

DETAILED DESCRIPTION OF THE INVENTION

The present invention is comprised of the use of novel tetrazolium salts that will reduce to blue or purple water soluble formazans.

The first general design of the present invention obtains new tetrazolium compounds having attached to the tetrazolium ring a naphthalenedisulfonic acid moiety. The naphthalenedisulfonic moiety provides a side chain having two acidic groups thereon for rendering the compound water soluble. For this purpose, tetrazolium compounds of the formula 3 have been synthesized

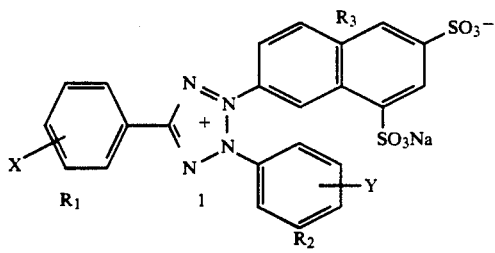

in which the $R_3$ group is a naphthalene with two sulfonate groups attached. Points of attachment of sulfonate groups and of tetrazolium nitrogen to the naphthalene ring may be varied. Two sulfonate groups are necessary for water solubility since tetrazolium zwitterions, like most large-molecule zwitterions, tend to be poorly soluble in water. However, unlike XTT which utilizes one acidic group (sulfonate group) on each of the two rings attached to nitrogen atoms of the central tetrazolium ring, the present invention provides a single side chain having two acidic groups thereon for rendering the compound water soluble. The other side chains thus are available for further modification to render the compound more useful.

The present invention provides means necessary for water solubility of the compound while also allowing for two other side chains which can be modified for providing a blue or purple color to the compound when reduced to the corresponding formazan. Moreover, the large conjugation of the naphthalene moiety contributes to the blue color of the formazans produced by reduction of the above mentioned compounds. Thus, the present invention provides means for gaining the water solubility of prior art compounds such as XTT but also renders the present invention more structurally flexible to overcome the problems of the XTT compound.

Tetrazolium compounds of the formula 3 were synthesized in the following manner. An aldehyde 4 was reacted with a hydrazine 5 to give the hydrazone 6. The hydrazone 6 was then reacted with the diazonium salt 7 to give the desired formazan 8. The formazan 8 was then oxidized to yield the desired tetrazolium compound 3.

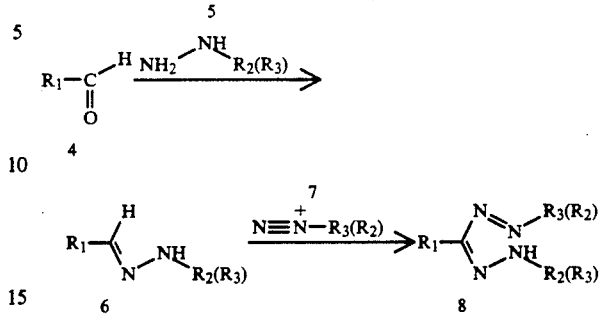

In addition to the tetrazolium compounds described above, the bis-tetrazolium compounds of the general formula 9 would be useful in cell viability assays in a fashion similar to the tetrazolium compounds. In particular, as part of the present invention, bis-tetrazolium compounds of the formula 10 would be synthesized by methods analogous to those leading to the tetrazolium compound 3.

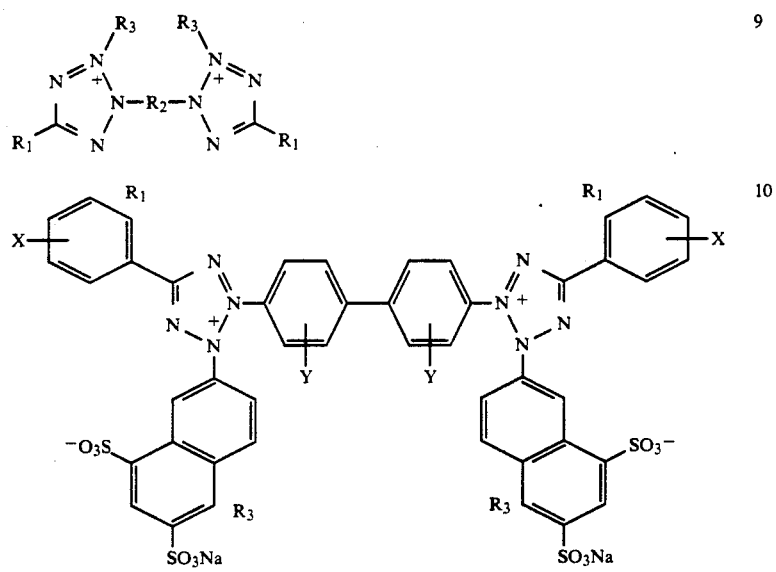

Those variants of the tetrazolium compound 3 and the bis-tetrazolium compound 10 which are useful in the present invention include those variants in which X can be a hydrogen, a nitro group, or a methoxy group; Y can be a hydrogen, a nitro group or a methoxy group; $R_1$ can be a pyridyl group or a methoxy-diiodophenyl group; $R_2$ can be a dimethylthiazolyl group or a benzothiazolylphenyl group: and $R_3$ is the previously mentioned naphthalene disulfonate group.

In the tetrazolium compounds 3 and 10, the naphthalene ring not only provides a carrier structure for the sulfonate groups and contributes to the ease of purification of the compounds, but it also enhances the color of the corresponding formazan, as in the case of known tetrazolium violet compounds. Virtually any desired color of formazan may be had by manipulating groups $R_1$ and $R_2$, since $R_3$ is capable of carrying both acidic groups. If both $R_1$ and $R_2$ are simple benzene rings, the formazan is crimson. The most preferred compound in the present invention has $R_1$=phenyl and $R_2$=4,5- dimethyl-2-thiazolyl. This particular formazan has an intense blue-purple color. Its tetrazolium zwitterion salt is smoothly reduced to the formazan in viable cell cultures dispersed in the usual media incorporating phenazine methosulfate as an electron carrier.

The naphthalenedisulfonate group is conveniently introduced by using as synthons the various aminonaphthalene disulfonic acids. Examples are 7-aminonaphthalene-1,3-disulfonic acid (Amido G Acid), 7-aminonaphthalene-2,4-disulfonic acid, and 3-aminonaphthalene-2,7-disulfonic acid (Amido R Acid). Also useful are aminonaphtholdisulfonic acids such as 4-amino-5-naphthol-2,7-disulfonic acid (H acid), 4-amino-5-naphthol-1,3-disulfonic acid (Chicago acid) and their O-methyl ethers. Using such synthons, the naphthalene disulfonate moiety may be introduced into the formazan and then into the tetrazolium salts in either of two ways. The aminonaphthalene disulfonic acid may be diazotized and the diazonium salt coupled with the appropriate hydrazone. Alternatively, the aminonaphthalene disulfonic acid may be converted into the corresponding hydrazinonaphthalene disulfonic acid which is condensed with the aldehyde to give a disulfonaphthylhydrazone, to which an appropriate diazonium salt then is coupled.

One particular advantage to using the aminonaphthalenedisulfonate and aminonaphtholdisulfonate synthons is that they are readily available commercially and are inexpensive. A second is that the formazans and tetrazolium salts of general structure exemplified by compounds 3 and 10 derived from them are more conveniently isolated and purified than are those based on aminobenzenedisulfonic acids. A third and most important advantage lies in the flexibility to adjust the structures of both of the other groups $R_1$ and $R_2$ attached to the tetrazolium core so as to optimize the color, redox potential and biological compatibility of the tetrazolium-formazan couple. Group $R_2$ may be phenyl, methoxyphenyl, dimethoxyphenyl, chlorophenyl, dichlorophenyl, bromophenyl, iodophenyl, naphthyl, butylphenyl, trifluoromethylphenyl, pyridyl, nitrophenyl, dimethyl-2-thiazolyl and other groups of the similar class. The variations of $R_2$ allow especially the adjustment of the color and redox potential. The 4,5-dimethyl-2-thiazolyl group is particularly valuable. Group $R_1$ may be phenyl, methoxyphenyl, nitrophenyl, diiodosalicyl, dimethylaminophenyl, methyl-2-thienyl, pyridyl, chorophenyl, chloronitrophenyl, trifluoromethylphenyl, naphthyl, and other groups of the similar class. Variations of $R_1$ allow especially the fine-tuning of redox potentials.

In a second general design of the present invention, one sulfonate group and one less acidic group such as oxyacetate or oxyphosphate are used. Particularly useful as the less acidic group is a phenoxyacetic acid group or a phosphomonoester grouping. It is preferred that the sulfonate group be attached to a benzene ring or a naphthalene ring, and that the oxyacetate or oxyphosphate group be attached elsewhere as exemplified in compound 11 and compound 12.

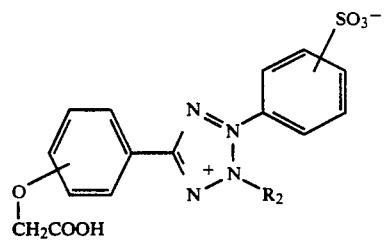

11

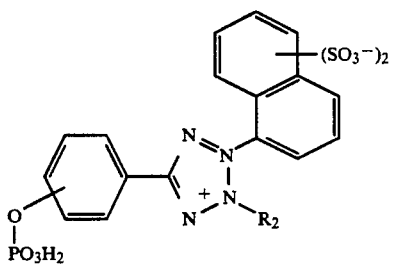

12

The point of attachment of the sulfonate group and the tetrazolium nitrogen to the benzene ring or the naphthalene ring may be varied, as may also the point of attachment of the other acidic group.

A benzenesulfonate group is conveniently introduced by using sulfanilic acid or metanilic acid. A naphthalenesulfonate group is conveniently introduced by using as synthons the various aminonaphthalenesulfonic acids such as 4-aminonaphthalene-1-sulfonic acid (naphthionic acid), 2-aminonaphthalene-1-sulfonic acid, 5-aminonaphthalene-2-sulfonic acid, 2-aminonaphthalene-8-sulfonic acid, 5-aminonaphthalene-1-sulfonic acid and 8-aminonaphthalene-1-sulfonic acid. Also useful are aminonaphtholsulfonic acids such as 4-amino-3-napthhol-1-sulfonic acid, 4-amino-5-naphthol-1-sulfonic acid, 6-amino-4-naphthol-2-sulfonic acid, 7-amino-4-naphthol-2-sulfonic acid, and their O-methyl ethers. Using these synthons, the arenesulfonate moiety may be introduced into the formazan and then into the tetrazolium salt in either of two ways. The aminosulfonic acid may be diazotized and the diazonium betaine coupled with the appropriate hydrazone. Alternatively, the aminosulfonic acid may be converted into the corresponding hydrazinoarenesulfonic acid which is condensed with the aldehyde to give the sulfohydrazone, to which an appropriate diazonium salt is then coupled. The aldehyde synthon bearing the less strongly acidic carboxylate or phosphate group is conveniently provided by p-hydroxybenzaldehyde or m-hydroxybenzaldehyde which may be carboxymethylated with chloroacetic acid or ethyl bromoacetate, or phosphorylated by means of phosphorus oxychloride and pyridine. The hydroxybenzaldehyde ring may carry additional substituents such as halogen, alkyl, alkoxyl and nitro, all of which serve to adjust the color, redox potential and biological compatibility of the tetrazolium-formazan couple. Group $R_2$ may be as previously described for variants of compounds 3 and 10, again to adjust the color and redox potential. The 4,5-dimethyl-2-thiazolyl group is particularly valuable.

An overwhelming advantage which tetrazolium salts of the second general design of the present invention possess over all other water-soluble tetrazolium-formazan couples (including those of the first general design of the present invention and others described in prior art and literature) lies in the ease with which they may be purified. Tetrazolium salts are stable to acids. In the presence of dilute mineral acids, the carboxylate and phosphate groups do not ionize significantly so that the compounds are simple betaines (zwitterions) having a single cationic and a single anionic charge. Hence they are sparingly soluble in water and readily crystallizable to purity from solvents such as aqueous acetonitrile. At physiological pH (7-7.5), however, as in cell cultures, enzyme assay buffers, etc., the carboxylate or phosphate group ionizes, so that the tetrazolium is now a di-anion mono-cation and is freely soluble in water as is necessary for its use. The formazan which results upon reduction is a di-anion, freely soluble in the aqueous culture medium or buffer. These inter-relationships are shown explicitly for the carboxylate compounds, and by implication for the phosphate compounds, in compounds 11, 11(a) and 11(b).

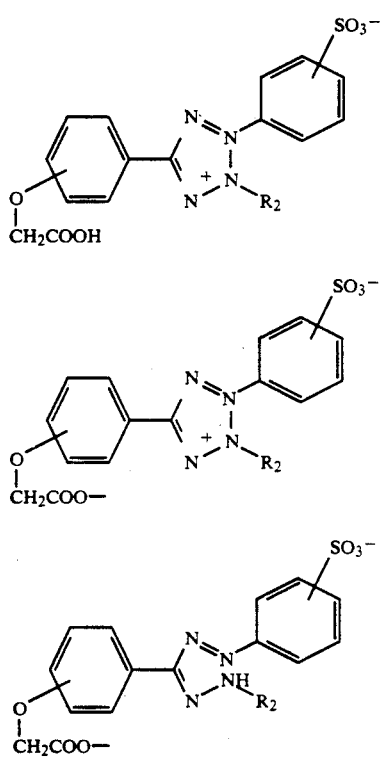

All of the tetrazolium salts of the present invention may be reduced to the corresponding formazans as, for example, by the treatment with a reducing agent such as formaldehyde at a pH of over 7, glyoxal at a pH of over 7, hydrazine hydrate, hydroxylamine, redox enzymes, cell cultures, polyhydric phenols, aromatic polyamines and aminophenols and the like.

The following examples illustrate detailed embodiments of the present invention but in no way limit the scope of the invention.

EXAMPLE 1

A solution of the monosodium salt of 7-naphthalenediazonium 1,3-disulfonic acid (0.3 g., prepared by diazotizing 7-aminonaphthalene-1,3-disulfonic acid with sodium nitrite) in water (5 ml.) was added dropwise to a stirred solution of benzaldehyde phenylhydrazone (0.19 g.) in pyridine (5 ml.) kept at 0° C. An intensely black-red solution resulted. Stirring was continued for 30 minutes at 0° C. Ice-cold half-saturated brine was added, followed by sufficient ice-cold hydrochloric acid (5 ml.) to dissolve the pyridine which oiled out. The precipitate of disodium 1,3-diphenyl-5-(7'-naphthyl) formazan-1',3'-disulfonate was collected by suction filtration, washed thoroughly with brine, and dried. Yield, 0.5 g.

A portion (0.28 g.) of the above formazan was dissolved in water (24 ml.) and treated with N-bromosuccinimide (0.1 g.) in ethyl acetate (5 ml.). Color was rapidly discharged. The pale yellow aqueous solution was extracted several times with ethyl acetate and then was shell-frozen and lyophilized. The crude monosodium 2,5-diphenyl-3-(7'-naphthyl) tetrazolium-1'3'-disulfonate (0.2 g.) thus obtained was recrystallized from methanolethanol mixture as a light yellowish-tan powder.

EXAMPLE 2

A solution of the monosodium salt of 7-naphthylhydrazine-1,3-disulfonic acid (8.5 g.) in water (50 ml.) was stirred with benzaldehyde (2.65 g.) and a few drops of acetic acid. After 90 minutes the homogeneous solution was diluted with pyridine (100 ml.) and methanol (150 ml.) containing sodium acetate trihydrate (14 g.). The mixture was chilled to −20° C. and stirred during the dropwise addition of a solution of 4,5-dimethyl-2-thiazolediazonium chloride (prepared by adding sodium nitrite (1.75 g.) dissolved in a little water to an ice-cold, stirred solution of 2-amino-4,5-dimethylthiazole hydrochloride (4.1 g.) in 50 ml. of 5-molarhydrochloric acid). The cooling bath was removed and the mixture was allowed to come spontaneously to room temperature. Saturated brine (50 ml.) now was added and organic solvents were removed by three extractions with 800-ml. portions of ether. Further addition of brine (200 ml.) completed precipitation of disodium 1-(4',5'-dimethyl-2'-thiazolyl)-3-phenyl-5-(7''-naphthyl)formazan-1'',3''disulfonate which was collected by suction filtration, washed thoroughly with brine, and dried. The crude product (3.95 g.) was 80% pure as indicated by its uv-vis spectrum, λmax (ethanol) 580 nm, εmax 15,000.

A portion (0.22 g.) of the above formazan was oxidized with N-bromosuccinimide as described in Example 1 above. The monosodium 2-(4',5'-dimethyl-2'-thiazolyl)-3-(7''-naphthyl)-5- phenyltetrazolium-1'',3''-disulfonate (0.17 g.) obtained was recrystallized from acetonitrile as a bright yellow powder.

EXAMPLE 3

A mixture of 4-formylphenoxyacetic acid (3.6 g.), phenylhydrazine-4-sulfonic acid (3.76 g.), sodium acetate trihydrate (3 g.) and water (30 ml.) was stirred and heated until it became homogenous. Upon cooling, the 4-sulfophenylhydrazine of 4-formylphenoxy-acetic acid crystallized as its sodium salt, yellow plates (6.0 g.).

A portion (3.73 g.) of this hydrazone salt was dissolved in a mixture of pyridine (20 ml.), methanol (20 ml.) and water (20 ml.). The solution was chilled to −10° C. and stirred during the dropwise addition of a solution of 4,5-dimethylthiazolediazonium chloride (prepared by adding sodium nitrite (0.7 g.) dissolved in a little water to an ice-cold stirred solution of 2-amino-4,5-dimethylthiazole hydrochloride (1.64 g.) in 10 ml. of 5-molar hydrochloric acid). The purple-black solution was allowed to come to room temperature, treated with saturated brine (40 ml.), and extracted repeatedly with ether to remove organic solvents. Neutralization with sodium bicarbonate and addition of further brine completed precipitation of the disodium salt of 1-(4',5'-dimethyl-2'-thiazolyl)-3-(4'''-carboxymethoxyphenyl)-5-(4''-sulfophenyl) formazan as a fine, dark blue-black solid. This was collected by suction filtration, washed thoroughly with brine, and dried. The crude product (3.25 g.) was 60% pure as indicated by its uv-vis spectrum, λmax (ethanol) 595 nm, ε max 11,200.

A portion (1.42 g.) of the above formazan was dissolved in water (60 ml.) and oxidized with bromine vapor entrained in a stream of nitrogen. The tetrazolium betaine, 2-(4',5'-dimethyl-2'-thiazolyl)-3-(4''-sulfophenyl)-5-(4'''-carboxymethoxyphenyl) tetrazolium, separated directly as a yellow solid during the course of oxidation, and more was recovered by concentrating the reaction solution. Purification was effected by dissolving the material (0.75 g.) in dilute sodium carbonate solution, filtering and reprecipitating with hydrochloric acid. Elemental analysis: Found, C, 49.07; H, 3.48; N, 14.28%. Calculated for C20H17N5O6S2,C, 49.27; H, 3.51; N, 14.37%. Ultraviolet-visible spectrum: λmax (water) 385 nm, εmax 7,600.

EXAMPLE 4

A mixture of 3-formylphenoxyacetic acid (5 g.), phenylhydrazine-4-sulfonic acid (5.22 g.), sodium acetate trihydrate (4.5 g.) and water (50 ml.) was stirred and heated until it become homogenous. Upon cooling and dilution with ethanol, the 4-sulfophenyl-hydrazone of 3-formylphenoxyacetic acid crystallized as its sodium salt (7.6 g.).

A portion (3.55 g.) of this hydrazone salt was dissolved in a mixture of pyridine (20 ml.), methanol (20 ml.) and water (40 ml.). The solution was chilled to −15° C. and stirred during the dropwise addition of a solution of 4,5-dimethylthiazolediazonium chloride (prepared by adding sodium nitrite (0.67 g.) dissolved in a little water to an ice-cold stirred solution of 2-amino-4,5-dimethylthiazole hydrochloride (1.57 g.) in 10 ml. of 5-molar hydrochloric acid). The purple-black solution was allowed to come to room temperature, treated with saturated brine (50 ml.), neutralized with sodium bicarbonate, and extracted repeatedly with ether to remove organic solvents. Addition of further brine completed precipitation of the disodium salt of 1-(4',5'-dimethyl-2'-thiazolyl)-3-(3''-carboxymethoxyphenyl) -5-(4'''-sulfophenyl) formazan as a dark blue-black solid. This was collected by suction filtration, washed thoroughly with brine, and dried. The crude product (3.7 g.) had uv-vis λmax (ethanol) 560 nm, ε11,500.

A sample (4.3 g.) of the above formazan was dissolved in water (300 ml.), chilled to 5'C., and oxidized with bromine (1 ml.) dissolved in acetonitrile (5 ml.). The tetrazolium betaine, 2-(4',5'-dimethyl-2'-thiazolyl)-3-(4''-sulfophenyl)- 5-(3'''-carboxymethoxyphenyl) tetrazolium, separated as a gelatinous yellow solid which changed to a filterable yellow solid (2.1 g.) upon heating to 50° C. Purification was effected by recrystallization from acetonitrile-water (2:1) mixture (150 ml.) containing a little bromine to prevent darkening by reversion to formazan. Elemental analysis: Found, C, 49.41; H, 3.55; N, 14.52%. Calculated for C20H17N5O6S2, C, 49.27; H, 3.51; N, 14.37%. Ultraviolet-visible spectrum: λmax (water) 380 nm, εmax 8,300.

Particularly useful novel compounds of the present invention include the compound 2-(4'5'-dimethyl-2'-thiazolyl)-3-(1'',3''-disulfo-7''-naphthyl-5-phenyltetrazolium, inner salt, sodium salt; the compound 2-(4',5',-dimethyl-2'-thiazolyl)-3-(4''-sulfophenyl)-5-(4'''-carboxymethoxyphenyl) tetrazolium, inner salt; and the compound 2-(4',5'-dimethyl-2'-thiazolyl)-3-(4''-sulfophenyl)-5-(3'''-carboxymethoxyphenyl) tetrazolium, inner salt.

The invention includes use of the foregoing tetrazolium compounds and reduction of such compounds into the corresponding water-soluble formazans in cell viability assays as well as in other bioassay procedures. The invention capitalizes on the water-solubility of the colored formazan produced upon reduction of the novel tetrazolium zwitterion-salt. As practiced, the dye diffuses out of the cells in which it is produced into the culture medium, optical density is read directly (the steps involving removal of the medium and extraction with solvent are obviated) and the method become amenable to full automation. The assay of the present invention is applicable against a wide range of human tumor cell lines. Its application to the screening of anti-AIDS drugs in no less significant.

This invention is clearly new and useful. moreover, it was not obvious to those of ordinary skill in the art at the time it was made, in view of the prior art considered as a whole.

It will thus be seen that the advantages set forth above, and those made apparent from the foregoing description, are efficiently attained and since certain changes may be made in the above construction without departing from the scope of the invention, it is intended that all matters contained in the foregoing description shall be interpreted as illustrative and not in a limiting sense.

Changes and modifications in the specifically described embodiments can be carried out without departing from the scope of the invention which is intended to be limited only by the scope of the appended claims.

It is also to be understood that the following claims are intended to cover all of the generic and specific features of the invention herein described, and all statements of the scope of the invention upon which, as a matter of language, might be said to fall therebetween.

What is claimed is:

1. A tetrazolium compound having attached as a side chain to the tetrazolium ring a naphthalene ring having two sulfonate groups thereon.

2. A compound as set forth in claim 1 wherein the side chain is 2-naphthyl-6, 8-disulfonate.

3. A tetrazolium compound having attached to the tetrazolium ring side chains having one sulfonate group and one group which is less acidic than the sulfonate group selected from the group consisting of oxyacetic acid group or phosphomonoester group, rendering said compound and the related formazan water soluble.

4. A tetrazolium compound of the formula

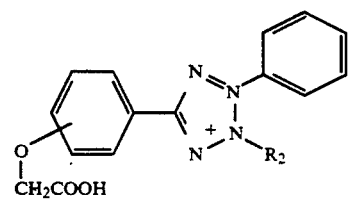

wherein R2 is 4,5-dimethyl-2-thiazolyl.

5. A tetrazolium compound of the formula

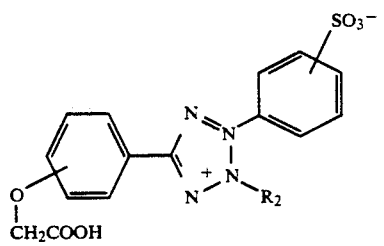
wherein R₂ is 4,5-dimethyl-2-thiazolyl.
6. Compound, 2-(4,40 ,5'-dimethyl-2'-thiazolyl-3-(1'',3''-disulfo-7''-naphthyl)-5-phenyltetrazolium, inner salt, sodium salt.
7. Compound, 2-(4',5'-dimethyl-2'-thiazolyl)-3-(4''-sulfophenyl)-5-(4'''-carboxymethoxyphenyl) tetrazolium, inner salt.
8. Compound 2-(4',5'-dimethyl-2'-thiazolyl)-3-(4''-sulfophenyl)-5(3''''-carboxymethoxyphenyl) tetrazolium, inner salt.
* * * * *